US00PP10038P

United States Patent [19]

Glicenstein

[11] Patent Number: Plant 10,038

[45] Date of Patent: Sep. 23, 1997

[54] CHRYSANTHEMUM PLANT NAMED 'GLOWING LYNN'

[75] Inventor: Leon Glicenstein, Salinas, Calif.

[73] Assignee: Yoder Brothers, Inc., Barberton, Ohio

[21] Appl. No.: 605,813

[22] Filed: Feb. 22, 1996

[51] Int. Cl.[6] ..... A01H 5/00

[52] U.S. Cl. ..... Plt./79

[58] Field of Search ..... Plt./76, 79

[56] References Cited

U.S. PATENT DOCUMENTS

| | | | |
|---|---|---|---|
| P.P. 8,171 | 3/1993 | VandenBerg | Plt./76 |
| P.P. 8,877 | 8/1994 | Glicenstein | Plt./76 |
| P.P. 8,892 | 9/1994 | Glicenstein | Plt./76 |
| 4,616,099 | 10/1986 | Sparkes | 47/58 |

OTHER PUBLICATIONS

Broertyes, et al., 1980, "A mutant of a mutant of a . . . Irradiation of progressive radiation-induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by x-rays", Am. Soc. Hart. Sci. Proc., pp. 613–620.

Broertjes, 1966 "Mutation breeding of chrysanthemums", Euphytica, 15:156–162.

Dowrick, et al., 1966, "The induction of mutations in chrysanthemum using x- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Glowing Lynn particularly characterized by its flat capitulum form; decorative capitulum type; greyed-orange ray floret color, with darker center of the flower; diameter across face of capitulum of 51 to 60 mm when fully opened; branching pattern is spreading and prolific, with 7 to 9 laterals developing after pinch when grown outside under natural daylength in fall flowerings; natural season flower date of August 27 to September 5 when planting rooted cuttings on June 17 to 21 in Salinas, Calif., and of September 20 to 30 when planting rooted cuttings June 15 to 18 in Hightstown, N.J.; plant height of 23 to 25 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar named Glowing Lynn.

Glowing Lynn, identified as 7978 (88–264Q01), is a product of a mutation induction program. The new cultivar was discovered and selected by inventor Leon Glicenstein on Sep. 1, 1993 in a controlled environment in Salinas, Calif. as one flowering plant within a flowering block established as rooted cuttings from stock plants which had been exposed as unrooted cuttings to an X-ray source of 2000 rads in Fort Myers, Fla. on Jan. 28, 1993. The irradiated parent cultivar was the cultivar Peachy Lynn, disclosed in U.S. Plant Pat. No. 8,892 and described as a flat decorative garden mum with peach-orange flower color with darker center of the flower.

The irradiation program resulting in Glowing Lynn had as its primary objective the expansion of color ranges of the cultivar Lynn, disclosed in U.S. Plant Pat. No. 8,171 and the parent cultivar Peachy Lynn. The irradiation program comprised irradiation of cuttings of the parent cultivar at irradiation levels of 1500, 1750 and 2000 rads. A total of 253 cuttings harvested from a total of 225 irradiated plants were planted on Jun. 21, 1993. Of these, 1 initial selection was made, which selection was then revegetated and reflowered. Three consecutive flowerings resulted in maintaining this selection as a PI (Possible Introduction) and was further trialed in Salinas, Calif., Hightstown, N.J. and Leamington, Ontario, Canada, ultimately resulting in the decision to introduce this selection as Glowing Lynn.

The first act of asexual reproduction of Glowing Lynn was accomplished when vegetative cuttings were taken from the initial selection in November of 1993 in a controlled environment in Salinas, Calif., by technicians working under supervision of Leon Glicenstein.

Horticultural examination of controlled flowerings of successive plantings has shown that the unique combination of characteristics as herein disclosed for Glowing Lynn are firmly fixed and are retained through successive generations of asexual reproduction.

Glowing Lynn has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Glowing Lynn, which, in combination, distinguish this Chrysanthemum as a new and distinct cultivar:

1. Flat capitulum form.
2. Decorative capitulum type.
3. Greyed-orange ray floret color, with darker center of the flower.
4. Diameter across face of capitulum of 51 to 60 mm when fully opened.
5. Branching pattern is spreading and prolific, with 7 to 9 laterals developing after pinch when grown outside under natural daylength in fall flowerings.

6. Natural season flower date of August 27 to September 5 when planting rooted cuttings on June 17 to 21 in Salinas, Calif., and of September 20 to 30 when planting rooted cuttings June 15 to 18 in Hightstown, N.J.

7. Plant height of 23 to 25 cm when grown in fall under natural daylength with no growth regulators.

8. Durable, uniform performance.

The accompanying photographic drawing is a color photograph of Glowing Lynn grown as a pinched garden mum under natural season outside conditions in Salinas, Calif., with the colors being as nearly true as possible with illustrations of this type. Plants were grown outside and dug and transplanted in 15 cm pots for photography purposes.

Of the commercial cultivars known to the inventor, the most similar in comparison to Glowing Lynn are the parent cultivar Peachy Lynn and the grandparent cultivar Lynn. All traits of Glowing Lynn are similar to those of Lynn and Peachy Lynn, except for the ray floret color. The ray floret color of Glowing Lynn is greyed-orange with darker center of the flower (RHS 168C to 168D), while the ray floret color of Lynn is described as light purple (RHS 75B, 75C), and the ray floret color of Peachy Lynn is peach-orange (RHS 179D for mature outer petals). Glowing Lynn is distinguished from Radiant Lynn, a mutation of Lynn disclosed in Plant Pat. No. 8,877, only by ray floret color.

In the following description color references are made to The Royal Horticultural Society Colour Chart. The color values were determined on plant material grown as a pinched garden mum grown outdoors in Salinas, Calif. on Sep. 1, 1995.

Classification:

*Botanical.*—*Dendranthema grandiflora* cv Glowing Lynn.

*Commercial.*—Flat decorative garden mum.

INFLORESCENCE

A. Capitulum:

*Form.*—Flat

*Type.*—Decorative.

*Diameter across face.*—51 to 60 mm when fully opened.

B. Corolla of ray florets:

*Color (general tonality from a distance of three meters.*—Greyed-orange with darker center of the flower.

*Color (upper surface).*—168C to 168D, with darker center of the flower.

*Color (under surface).*—179D, streaked with 178C.

*Shape.*—Cross-section of young ray florets concave, longitudinal section of outer ray florets convex. Ray floret tips emarginate.

C. Corolla of disc florets:

Color (mature).—9A.

Color (immature).—144C.

D. Reproductive organs:

*Androecium.*—Present on disc florets only; very few, no pollen.

*Gynoecium.*—Present on both ray and disc florets.

PLANT

A. General appearance:

*Height.*—23 to 25 cm when grown in fall under natural daylength with no growth regulators.

*Branching pattern.*—spreading and prolific, with 7 to 9 laterals developing after pinch when grown outside under natural daylength in fall flowerings.

B. Foliage:

*Color (upper surface).*—147A.

*Color (under surface).*—147B.

*Shape.*—Small, lobed, slightly serrated.

What is claimed is:

1. A new and distinct Chrysanthemum plant named Glowing Lynn, as described and illustrated.

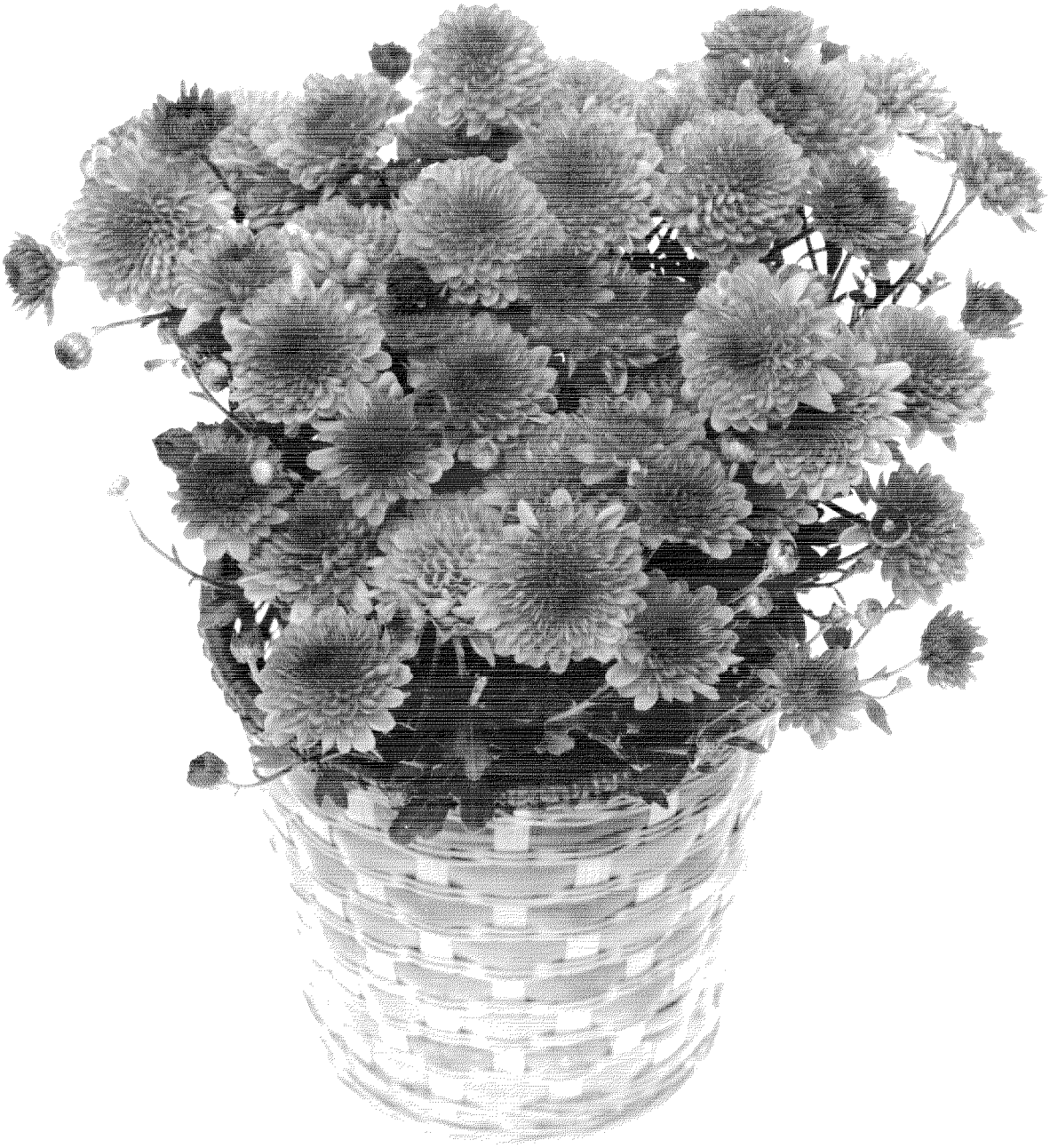

* * * * *